(12) United States Patent
Kibrya et al.

(10) Patent No.: US 11,678,915 B2
(45) Date of Patent: Jun. 20, 2023

(54) RATCHET RETRACTING HANDLES AND METHODS OF USING THE SAME

(71) Applicant: NuVasive, Inc., San Diego, CA (US)

(72) Inventors: Naomi Kibrya, San Diego, CA (US); John Love, San Diego, CA (US); Matthew Tobias Jacobs, San Diego, CA (US); Ryan Woods, San Diego, CA (US); Megan Jeffords, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 17/412,613

(22) Filed: Aug. 26, 2021

(65) Prior Publication Data

US 2022/0061895 A1    Mar. 3, 2022

Related U.S. Application Data

(60) Provisional application No. 63/071,956, filed on Aug. 28, 2020.

(51) Int. Cl.
*A61B 17/70*    (2006.01)
*A61B 17/00*    (2006.01)

(52) U.S. Cl.
CPC ..... *A61B 17/7082* (2013.01); *A61B 2017/00407* (2013.01)

(58) Field of Classification Search
CPC ............ A61B 17/7082; A61B 17/7076; A61B 2017/7077; A61B 17/7079; A61B 17/8888; A61B 17/8894; A61B 17/8897; A61B 2017/00469; A61B 2017/00407
See application file for complete search history.

(56) References Cited

U.S. PATENT DOCUMENTS

| | | | |
|---|---|---|---|
| 2007/0162046 A1 | 7/2007 | Vandewalle | |
| 2009/0275954 A1 | 11/2009 | Phan et al. | |
| 2014/0276894 A1 | 9/2014 | Ramsay et al. | |
| 2018/0368893 A1* | 12/2018 | DiVincenzo | A61B 17/7082 606/86 A |
| 2019/0125421 A1* | 5/2019 | Smith | A61B 17/8875 606/104 |
| 2019/0183516 A1* | 6/2019 | Peterson | A61B 17/1757 606/96 |
| 2019/0262055 A1* | 8/2019 | Haziza | A61B 17/8875 606/104 |
| 2019/0269469 A1* | 9/2019 | Bush, Jr. | A61B 34/20 606/86 A |

OTHER PUBLICATIONS

International Search Report and Written Opinion from corresponding application PCT/US2021/047678 dated Dec. 23, 2021, 18 pages.

\* cited by examiner

*Primary Examiner* — Jan Christopher L Merene
*Assistant Examiner* — Allie D Cline
(74) *Attorney, Agent, or Firm* — Hoffman Warnick LLC

(57) ABSTRACT

Disclosed herein are ratchet retracting handles and related methods for automatically retracting a stylet during insertion of a bone anchor.

20 Claims, 13 Drawing Sheets

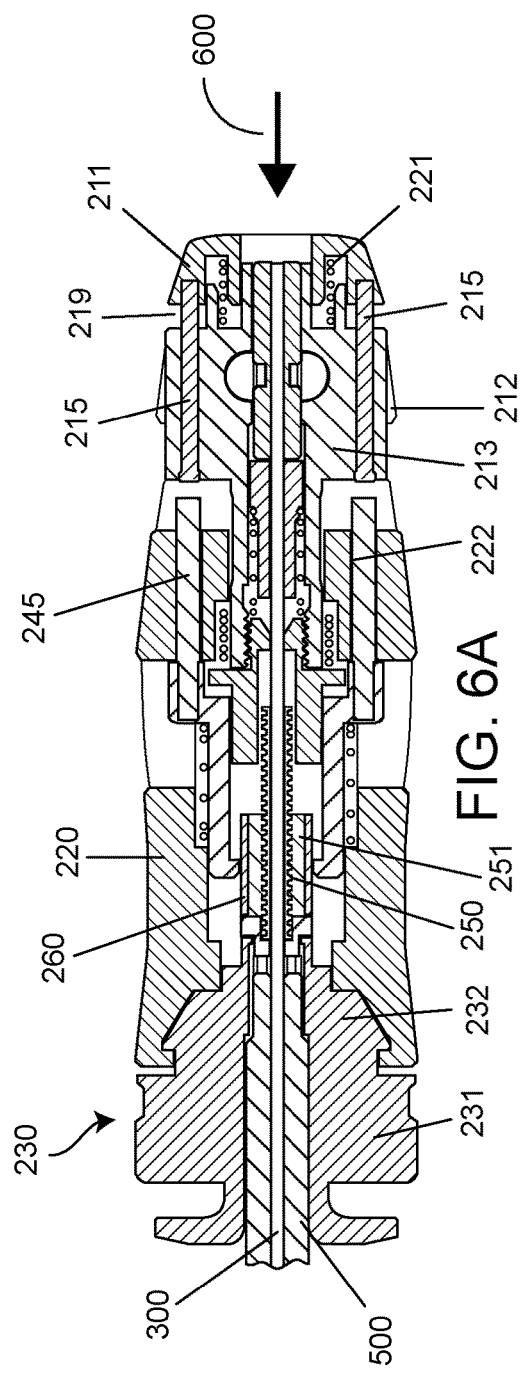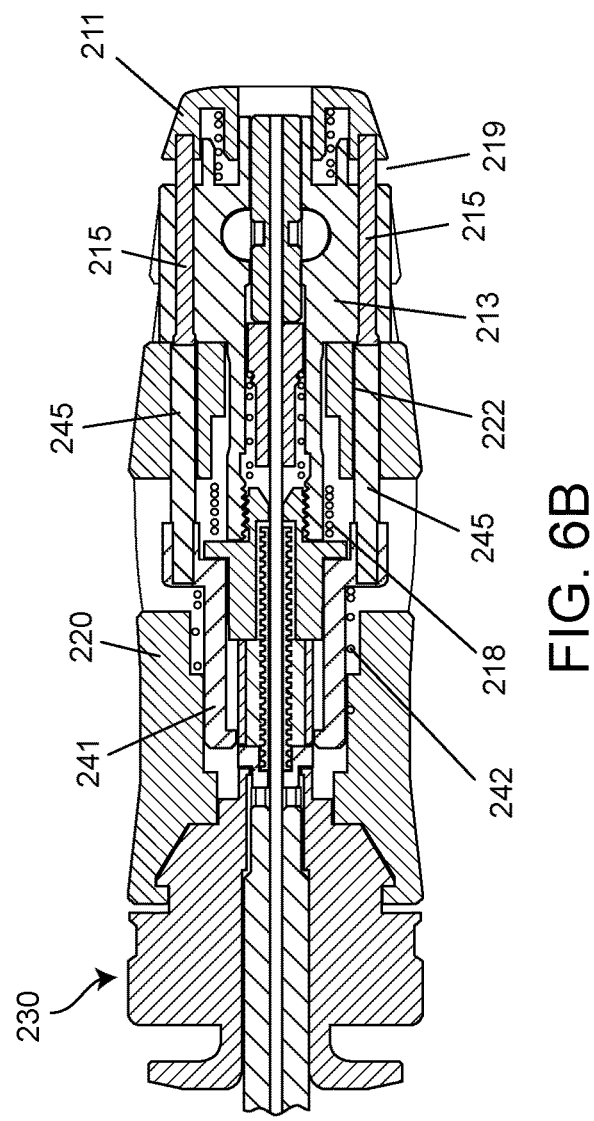

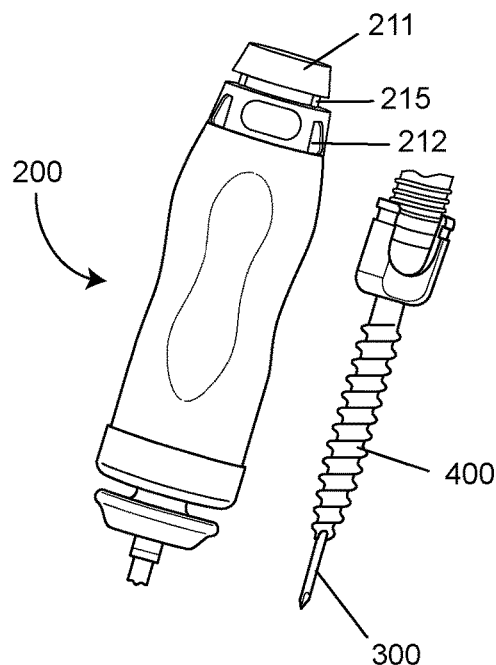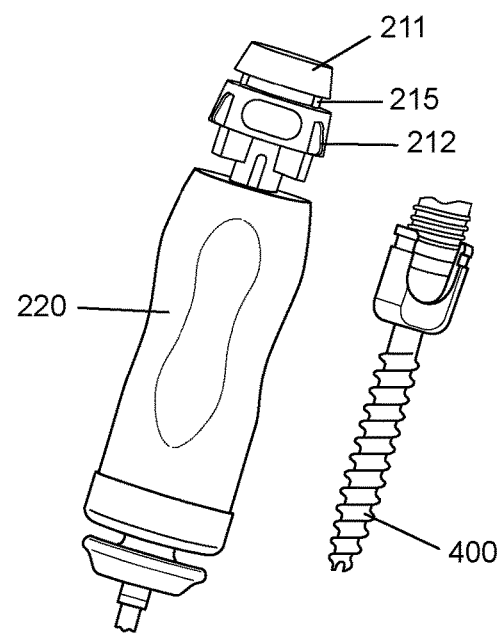
FIG. 10A  FIG. 10B
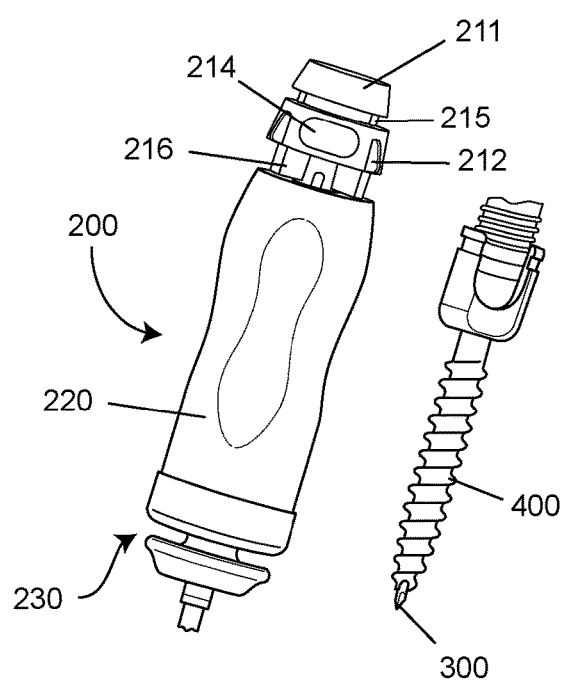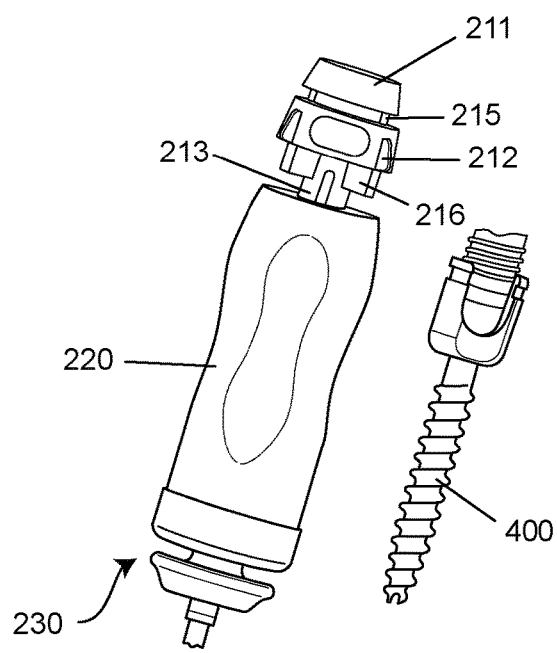
FIG. 11A  FIG. 11B

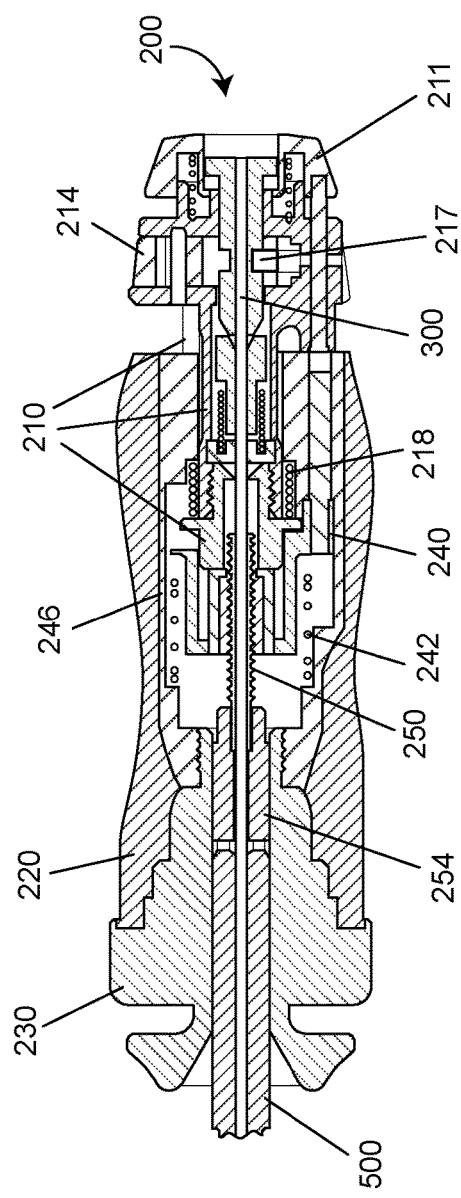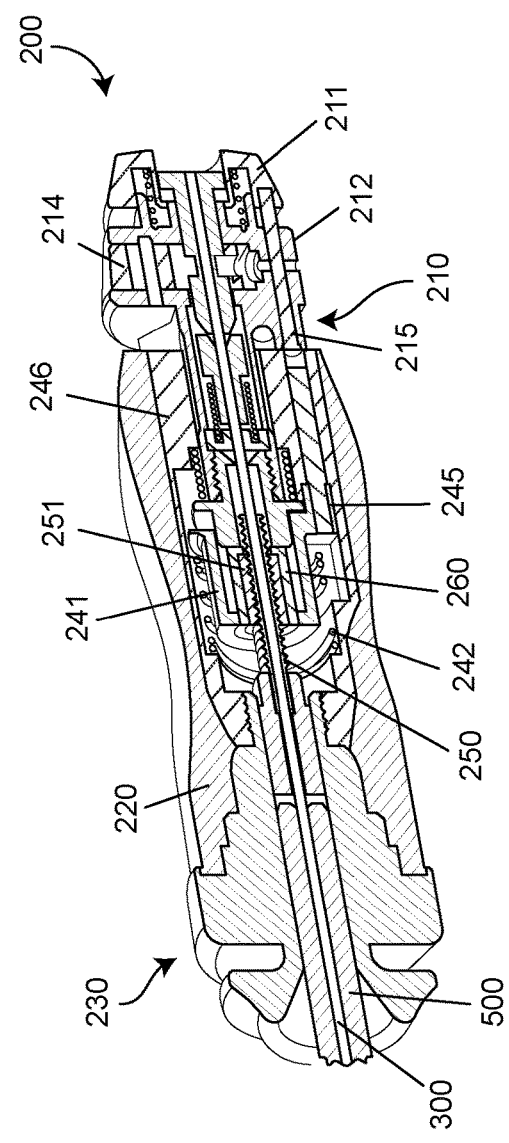
FIG. 12A
FIG. 12B

RATCHET RETRACTING HANDLES AND METHODS OF USING THE SAME

CROSS REFERENCE TO RELATED APPLICATION

This patent application claims the benefit of U.S. Provisional Patent Application Ser. No. 63/071,956, filed on Aug. 28, 2020, which is incorporated by reference as though fully set forth herein.

BACKGROUND OF THE DISCLOSURE

The spine is critical in human physiology for mobility, support, and balance. Spinal injuries can be debilitating or catastrophic to patients. Even small irregularities in the spine can cause devastating pain and loss of coordination.

Surgical procedures are commonly performed to correct problems with displaced, damaged, or degenerated intervertebral discs in the spine. A wide spectrum of spinal procedures involve the insertion of bone anchors. The accurate and efficient insertion of such bone anchors may be facilitated by the use of a stylet that extends beyond the distal tip of the bone anchor. Stylets may assist in avoiding screw skiving, and in planning insertion trajectory. However, existing stylets have demonstrated limitations with respect to ease of manipulation and retraction by the surgeon, and interference with screw insertion.

BRIEF DESCRIPTION OF THE INVENTION

According to a first aspect, a ratchet retracting handle is provided for automatically retracting a stylet during insertion of a bone anchor. In embodiments according to this aspect, the ratchet retracting handle comprises: a cap assembly translationally fixed to the stylet; a retractor assembly engaged with the cap assembly and disposed distally thereof, wherein engagement of the retractor assembly with the cap assembly produces translational movement of the retractor assembly in a distal direction; a lead screw rotatably coupled with the retractor assembly; a ratchet assembly comprising a ratchet knob and a ratchet body, the ratchet body being coupled to a distal end of the lead screw and to a proximal end of the screw driver; and a cover disposed over and rotationally fixed to the retractor assembly. In such embodiments, due to the ratcheting relationship between ratchet body and ratchet knob, rotation of the cover in a first direction is configured to advance the stylet and the bone anchor distally, while rotation of the cover in a second direction, opposite the first direction, is configured to retract the retractor assembly and the stylet proximally relative to the bone anchor, while the bone anchor is restrained from rotating.

According to a second aspect, an insertion and retraction assembly is provided for inserting a bone anchor and retracting a stylet. In embodiments according to this aspect, the insertion and retraction assembly comprises: a ratchet retracting handle comprising: a cap assembly translationally fixed to the stylet; a retractor assembly engaged with the cap assembly and disposed distally thereof, wherein engagement of the retractor assembly with the cap assembly produces translational movement of the retractor assembly in a distal direction; a lead screw coupled with the retractor assembly; a ratchet assembly comprising a ratchet knob and a ratchet body, the ratchet body being coupled to a distal end of the lead screw; a screw driver coupled at a proximal end thereof to the ratchet body; and a cover disposed over and rotationally fixed to the retractor assembly. Due to the ratcheting relationship between the ratchet body and the ratchet knob, rotation of the cover in a first direction is configured to advance the stylet and the bone anchor distally, while rotation of the cover in a second direction, opposite the first direction, is configured to retract the retractor assembly and the stylet proximally relative to the bone anchor, while the bone anchor and the screw driver are restrained from rotating.

According to a third aspect of the invention, a method is provided for inserting a bone anchor and automatically retracting a stylet associated with the bone anchor, the method comprising: providing a ratchet retracting handle, wherein the ratchet retracting handle comprises: a cap assembly translationally fixed to the stylet; a retractor assembly engaged with the cap assembly and disposed distally thereof, wherein engagement of the retractor assembly with the cap assembly produces translational movement of the retractor assembly in a distal direction; a lead screw rotatably coupled with the retractor assembly; a ratchet assembly comprising a ratchet knob and a ratchet body, wherein the ratchet body is coupled to a distal end of the lead screw; and a cover disposed over and rotationally fixed to the retractor assembly. The ratchet retracting handle may then be coupled to a driver of the bone anchor. The method further comprises rotating the cover in a first direction to advance the stylet and the bone anchor in the distal direction; and rotating the cover in a second direction, opposite the first direction, to restrain the bone anchor from rotating and simultaneously retract the retractor assembly and the stylet proximally relative to the bone anchor.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIG. 6A provides a cross-sectional view corresponding to the perspective view of FIG. 5A, and illustrates the ratchet retracting handle in the docking mode and beginning the transition to the extended mode, according to an embodiment of the invention.

FIG. 6B provides a cross-sectional view corresponding to the perspective view of FIG. 5B, and illustrates the ratchet retracting handle starting extension of the stylet, according to an embodiment of the invention.

FIGS. 10A and 10B provide perspective views of the ratchet retracting handle in the extended mode with the stylet extended and retracted, respectively.

FIGS. 11A and 11B provide perspective views of the ratchet retracting handle in the docking mode with the stylet extended, and retracted, respectively.

FIGS. 12A and 12B provide cross-sectional and cutaway views, respectively, of a ratchet retracting handle according to an embodiment of the invention.

Figure 1A:
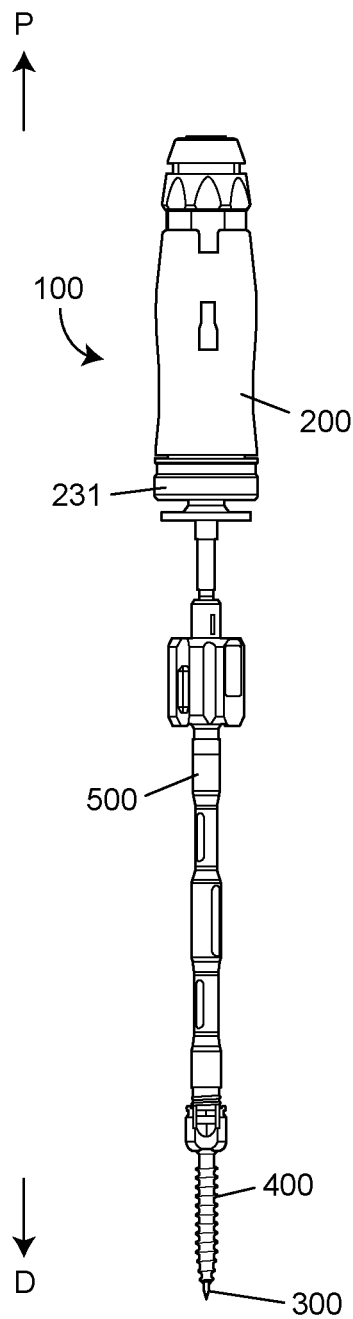
FIGS. 1A-1B provide side views of a ratchet retracting handle coupled with a driver, a bone anchor, and a stylet according to an embodiment of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

Figure 1B:
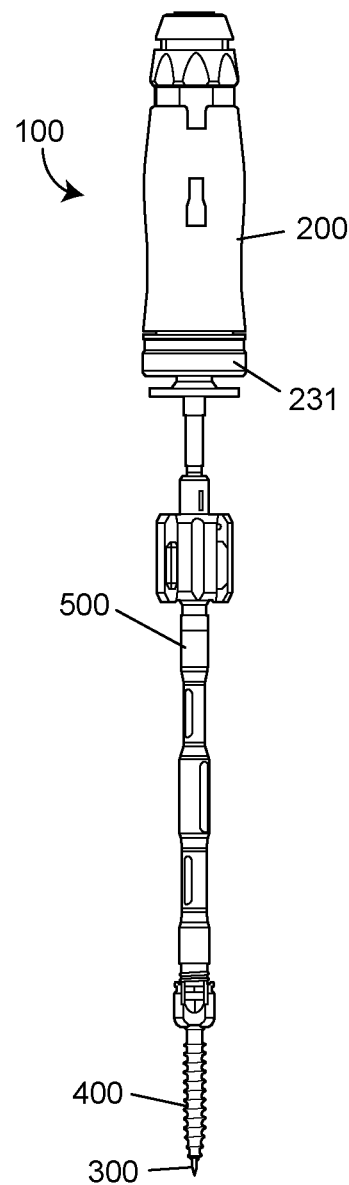
Figure 1C:
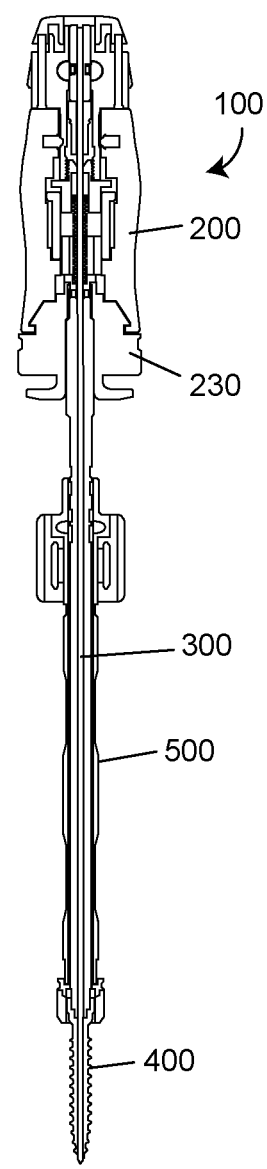
FIG. 1C provides a cross-sectional view of a ratchet retracting handle coupled with a driver, a bone anchor, and a stylet according to an embodiment of the invention.

As indicated above and as illustrated in FIGS. 1A-1C, aspects of the invention provide a ratchet retracting handle 200 for use in an insertion and retracting assembly 100 for the insertion of a bone anchor 400 into a bone. Ratchet retracting handle 200 may include integrated mechanisms as described further herein to manage the retention, deployment, and retraction of a stylet 300, and allow the user to fix the protrusion of the stylet 300 from the tip of the screw 400, and mallet or push on the proximal end of ratchet retracting handle 200 to extend the stylet 300 in a distal direction. During or after the insertion of screw 400, the ratcheting mechanism of the handle 200 may be used to automatically retract the stylet 300.

Embodiments of the ratchet retracting handle 200 disclosed herein advantageously facilitate automatic retraction of stylet 300, which can be conveniently and efficiently achieved using only one hand, e.g., by rotating handle 200. The distance of retraction can be pre-determined, e.g., stylet 300 may be retracted a predetermined distance sufficient to withdraw the tip of the stylet from within a patient during a procedure. Further, ratchet retracting handle 200 may provide a surgeon with improved flexibility by facilitating retraction of stylet 300 in both a docking mode and an extended mode.

As disclosed herein, the term bone anchor is used interchangeably with, and is considered equivalent to and synonymous with the terms: bone fastener, fastener, fixation screw, spinal fixation screw, bone screw, and pedicle screw. The term driver is used interchangeably with, and is considered equivalent to and synonymous with a screw driver, or any device that drives insertion of a bone anchor as would be understood by one skilled in the art. The term stylet is used interchangeably with, and is considered equivalent to the terms, k-wire, guide wire, and wire. Use of the term proximal refers to the direction away from attachment of an element to the subject, shown in FIG. 1A as direction P, while use of the term distal refers to the direction opposite the proximal direction and toward attachment of an element to the subject, shown in FIG. 1A as direction D.

With reference to FIGS. 1A-1C, an insertion and retraction assembly 100 is provided, including a ratchet retracting handle 200 as discussed above. Assembly 100 is provided for use in the insertion and fixation of bone anchors 400 into a bony structure such as, e.g., a vertebra, and for automatically retracting stylet 300 during or after such insertion of a bone anchor 400.

Figure 2A:
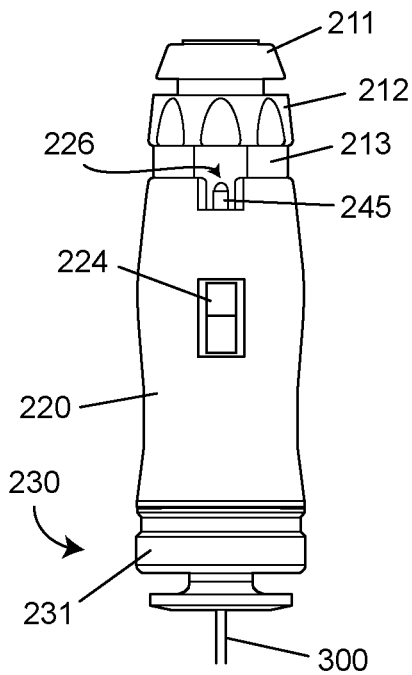
FIGS. 2A-2B provide side views of the ratchet retracting handle according to an embodiment of the invention.
Figure 2B:
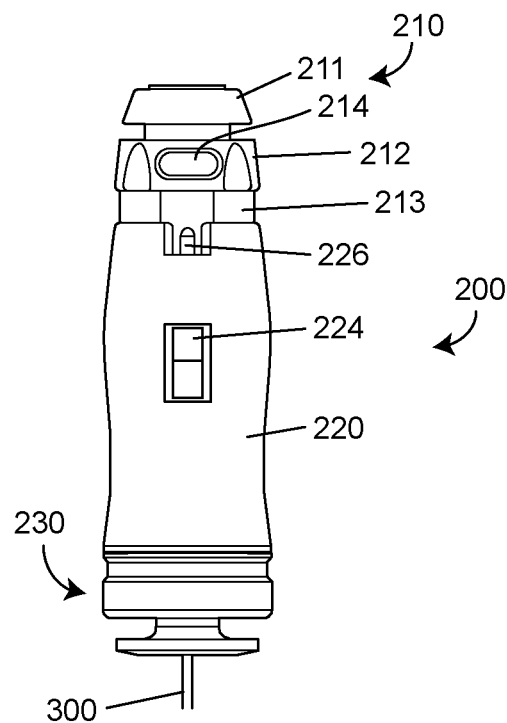
Figure 3A:
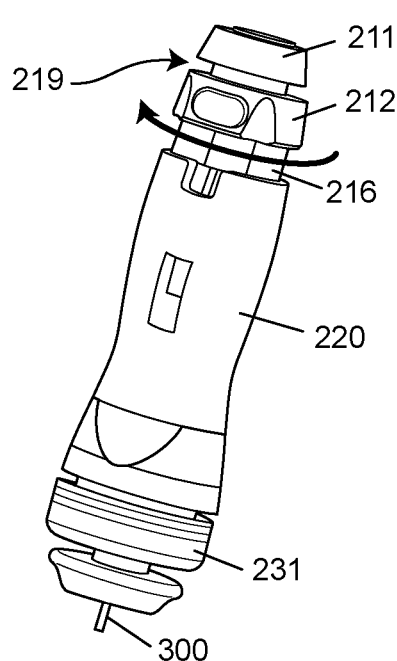
FIGS. 3A-3B provide perspective views of the ratchet retracting handle in a docking mode and an extended mode, respectively, according to an embodiment of the invention.
Figure 3B:
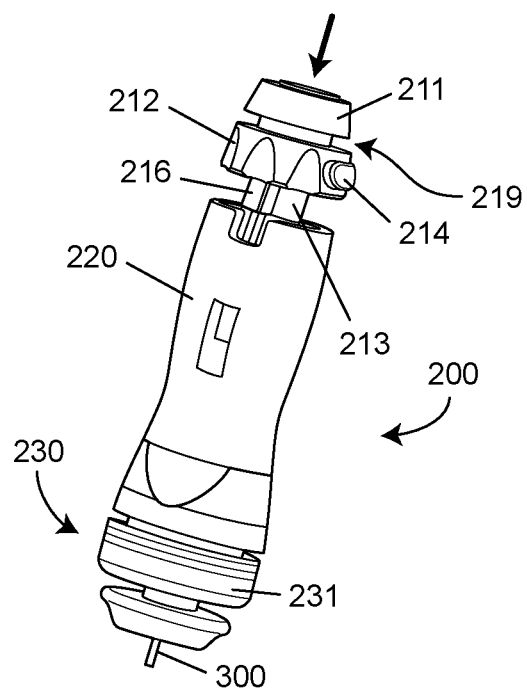

Handle 200 may be movable between a first mode and a second mode of operation, e.g., a docking mode and a deployed or extended mode. In the docking mode, stylet 300 may be retained at a fixed protrusion amount from the tip of bone screw 400 (see, e.g., FIG. 11A). The fixed protrusion amount may be, e.g., about 0.1 mm to about 5 mm, and more particularly may be about 0.1 mm, about 0.5 mm, about 1 mm, about 2 mm, about 3 mm, about 4 mm, or about 5 mm. When in the docking mode, stylet 300 remains at this fixed protrusion amount relative to the tip of bone anchor 400 even when malleting or pushing is applied to cap 211 (FIGS. 2A-2B) at the proximal end of handle 200. The fixed protrusion of stylet 300 from screw 400 may advantageously allow the surgeon to dock the screw 400 and stylet 300 on the bone without the screw 400 skiving off the bony surface. When the handle 200 is in the extended mode, handle 200 may allow translation of the stylet relative to the screw 400 to facilitate extension of stylet 300 past not only a distal tip of bone screw 400 but also past the fixed point in the docking mode. The transition from docking mode to extended mode unlocks the translation of stylet 300 relative to bone screw 400. Malleting or pushing on cap 211 of handle 200 in the extended mode extends stylet 300 distally for a predetermined distance, e.g., an additional 7 mm. In one example, stylet 300 may extend beyond the tip of bone anchor 400 by about 3 mm, and may extend an additional 7 mm in the extended mode, for a total distance of 10 mm in the extended mode. In other embodiments, however, the total extension of the tip of stylet 300 in the extended mode may be about 3 mm to about 10 mm beyond the tip of bone screw 400, or more particularly, about 3 mm, about 4 mm, about 5 mm, about 6 mm, about 7 mm, about 8 mm, about 9 mm, or about 10 mm beyond the tip of bone screw 400.

The practice of extending stylet 300 past the distal tip of bone screw 400 can advantageously allow the surgeon to confirm the trajectory of screw 400, e.g., under fluoroscopy, before deploying the screw 400 into bone. In the extended mode, as the screw 400 is deployed into bone, the backwards ratchet mechanism of the handle 200 may advantageously pull stylet 300 back to a retracted position. Thus, screw 400 is inserted and stylet 300 is retracted in simultaneous actions.

If desired, the user can mallet or push again on cap 211 of handle 200 to re-deploy stylet 300, and when inserting screw 400, stylet 300 may retract again using the ratchet mechanism. Methods of advancing stylet 300 distally other than malleting may also be used, including threaded and spring loading mechanisms. Methods of facilitating forward advancement of stylet 300 besides the overrunning thread can be used, including a threaded, ball-detent "quick-release."

Referring again to FIGS. 1A-1C, ratchet retracting handle 200 may have an elongated body extending axially along a longitudinal axis (not shown), and in a proximal to distal direction, and may be configured to be coupled to a proximal portion of screw driver 500 for inserting bone anchor 400 into bone during a surgical procedure. Stylet 300 may be coupled at a proximal end thereof to handle 200 (FIG. 1C), and may extend longitudinally within and through screw driver 500 and through a central, longitudinal cavity of bone anchor 400. Driver 500, bone anchor 400, stylet 300, and handle 200 may all be substantially coaxial. A distal tip of stylet 300 may be adjustably extended beyond the distal tip of bone anchor 400.

With reference to FIGS. 2A-2E and 3A-3B, ratchet retracting handle 200 is illustrated in greater detail. Ratchet retracting handle 200 may include a cap assembly 210 comprising a cap 211, a knob 212, and a cap body 213. Cap body 213 may include a distal portion that may be substantially annularly shaped, and a proximal portion that couples to knob 212. Knob 212 may be disposed proximally relative to cap body 213 and coupled thereto, and may be configured to rotatably control or initiate transitions of the ratchet retracting handle 200 between a docking mode and an extended mode, as discussed further herein. Cap 211 may be disposed at a proximal end of cap assembly 210, and may be matingly engaged with a proximal end of knob 212, as discussed further herein. Knob 212 may further include a retention button 214 disposed thereon, that controls operation of retention element 217 (FIG. 2E) disposed within knob 212. Retention element 217 is configured to releasably retain stylet 300 within knob 212, and maintain stylet 300 fixed in its translational position with respect to knob 212, described further below.

Figure 2C:
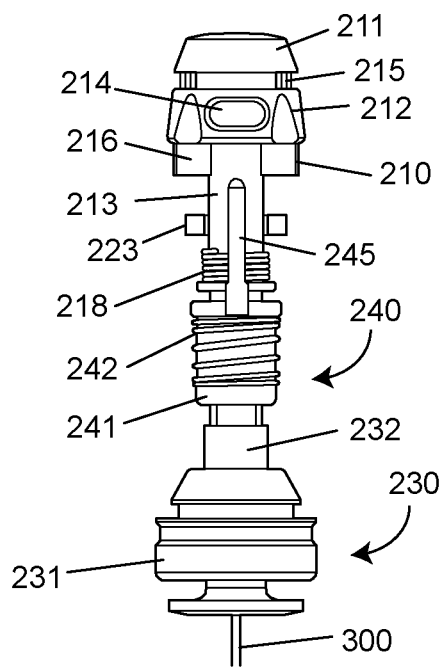
FIGS. 2C-2D provide side views of the cap assembly, the retractor assembly, and the ratchet assembly of the ratchet retracting handle according to an embodiment of the invention.
Figure 2D:
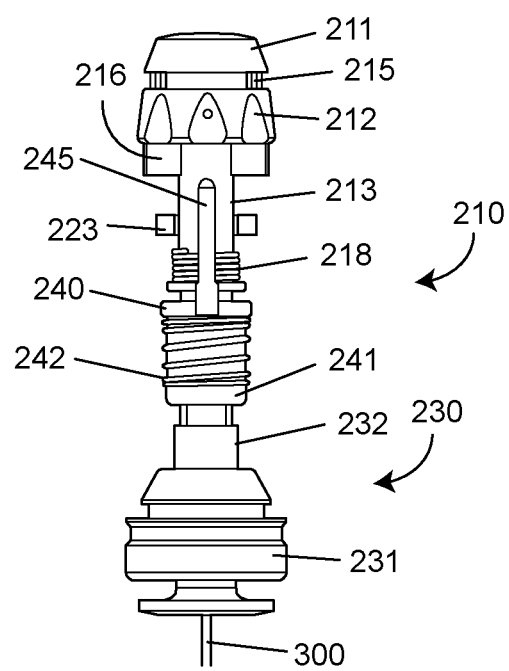

As shown in FIGS. 2C and 2D, cap 211 may further include two or more pushing posts 215, each of which extends distally from cap 211. Some particular embodiments may include, e.g., two pushing posts 215 as shown in FIG. 4B, or three pushing posts 215, or four pushing posts 215, or more. Cap body 213 may further include one or more legs 216, disposed distally of knob 212. Each leg 216 may extend a distance in a direction radially outward relative to the longitudinal axis of the device, and substantially perpendicular to a longitudinal axis of cap body 213 and handle 200. The distance extended radially outwardly by each leg 216 is such that each leg 216 may be securely received in a complementary-shaped extension channel 226 in a cover 220, as discussed further herein. Each leg 216 may further have a height that substantially corresponds to the depth of the corresponding extension channel 226. As shown in, e.g., FIGS. 4B-4C, pushing posts 215 may extend distally from cap 211 through legs 216. Cap assembly 210 may further include a cap assembly spring 218 disposed on the distal portion of cap body 213. In particular, spring 218 may be coiled around an outer surface, e.g. an outer circumferential surface, of the distal portion of cap body 213. Cap assembly spring 218 may be configured to bias or move stylet 300 in a distal direction relative to cap assembly 210, and participates in the advancement of stylet 300. The advantages and functions of pushing posts 215, leg 216, and spring 218 are discussed further below.

Figure 13:
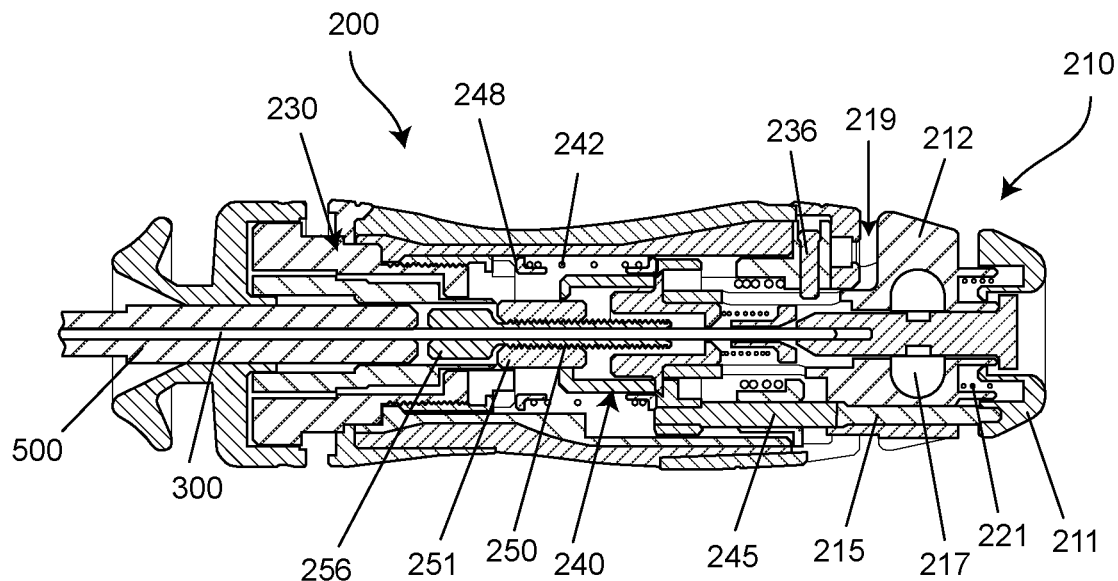
FIG. 13 provides a cross sectional view of a ratchet retracting handle, according to an embodiment of the invention.

With further reference to FIGS. 2C-2D, ratchet retracting handle 200 may also include a retractor assembly 240 coupled to cap body 213 at a distal end thereof. Retractor assembly 240 may include a retractor body 241, which may be substantially annular in shape. Retractor body 241 may include one or more retractor posts 245 extending proximally from a proximal end of retractor body 241. In some embodiments, the number of retractor posts 245 may be two, as illustrated in, e.g., FIG. 4B, however other embodiments may include other numbers of retractor posts 245 extending proximally from retractor body 241, e.g., retractor assembly 240 may include one, two, three, or more retractor posts 245. In embodiments having two or more retractor posts 245, the retractor posts 245 may be evenly spaced around a circumference of the proximal end of retractor body 241. For example, in embodiments having two retractor posts 245, the retractor posts may be disposed approximately 180 degrees apart along the circumference of the proximal end of retractor body 241, such that the two retractor posts 245 are on approximately opposite sides of the longitudinal axis from one other, as shown in FIG. 4B. In embodiments having three retractor posts 245, the retractor posts may be disposed approximately 120 degrees apart along the circumference of the proximal end of retractor body 241, such that the three retractor posts 245 are approximately equally spaced around an outer circumference of the proximal end of retractor body 241. A retractor spring 242 may be disposed over retractor body 241 such that retractor spring 242 may be coiled around an outer surface of the retractor body 241 (FIGS. 2C-2D), e.g., around an outer circumferential surface of retractor body 241. Retractor spring 242 may be biased such that it functions to retract stylet 300 in a proximal direction, thereby participating in the retraction of stylet 300 as described further herein. Certain embodiments, as illustrated in FIG. 13, may further include a bushing or washer 248. Bushing or washer 248 is a substantially rigid annular member that reduces the area for retractor spring 242, and thereby acts to prevent retractor spring 242 from being canted within handle 200. Thus, bushing or washer 248 may contribute to the avoidance of undesired binding of the assembly during operation of certain embodiments.

Figure 2E:
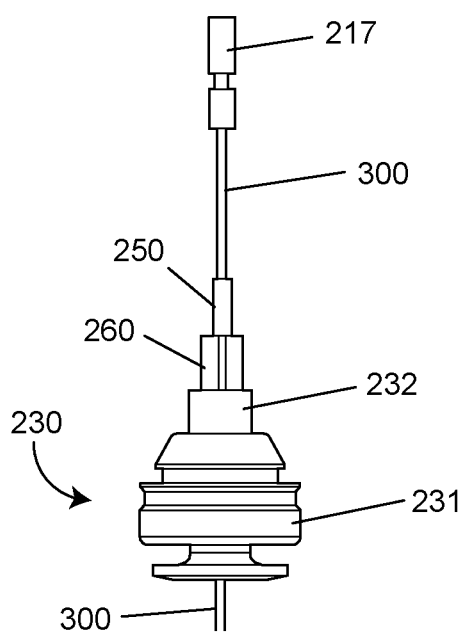
FIG. 2E provides a side view of the ratchet assembly, the lead screw, the sleeve of the ratchet retracting handle, and the stylet according to an embodiment of the invention.
Figure 7A:
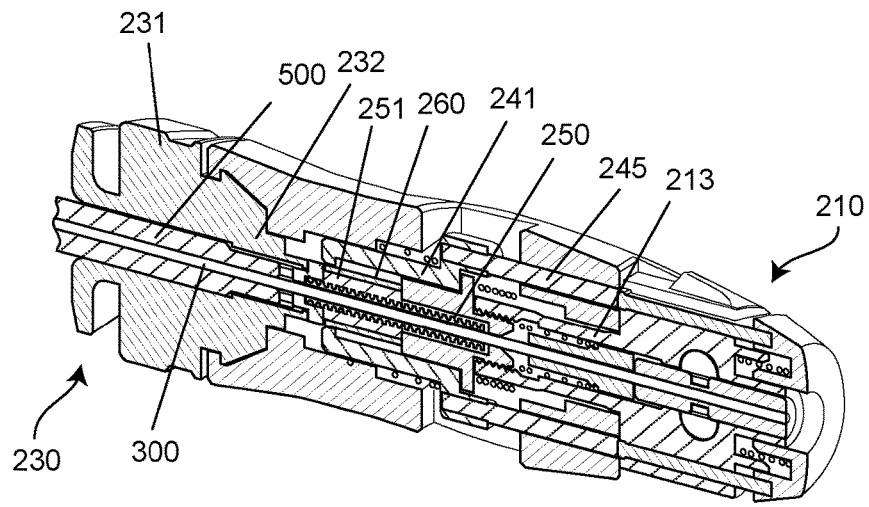
FIG. 7A provides a cutaway view of the ratchet retracting handle during stylet retraction, according to an embodiment of the invention.
Figure 7B:
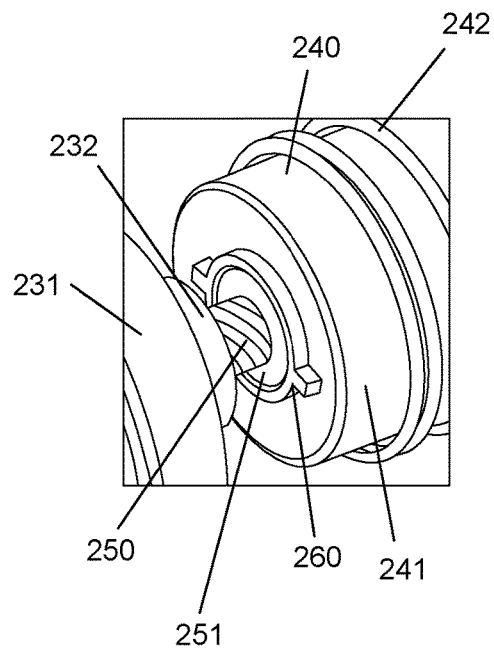
FIG. 7B provides a perspective view of a portion of the ratchet retracting handle during stylet retraction, according to an embodiment of the invention.
Figure 7C:
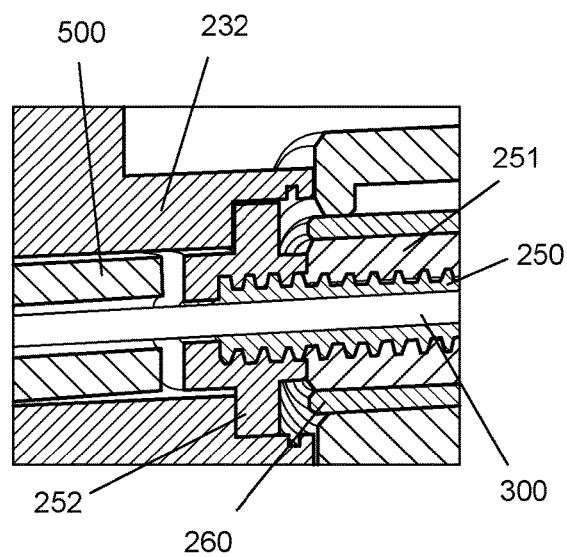
FIG. 7C provides a cross-sectional view of a portion of the ratchet retracting handle during stylet retraction, according to an embodiment of the invention.

Referring back to FIGS. 2A-2E and 3A-3B, ratchet retracting handle 200 may further include a ratchet assembly 230 that includes a ratchet knob 231 and a ratchet body 232. Ratchet knob is movable, e.g., rotatable, relative to ratchet body 232. As shown in FIG. 2E, ratchet body 232 is coupled to and rotationally fixed to lead screw 250. In some embodiments, ratchet body 232 may be coupled to lead screw 250 via lead screw attachment 252, as shown in, e.g., FIGS. 7A-7C. In other embodiments, ratchet body 232 may be coupled to lead screw 250 via an integrally formed ratchet body attachment 256, which may be integrally formed with lead screw 250, as shown in FIG. 13. This configuration provides an alternative to the use of lead screw attachment 252 as discussed herein. In either case, lead nut 251 may be coupled on lead screw 250, and sleeve 260 may be disposed over at least part of lead nut 251 (FIG. 4B). Lead nut 251 and sleeve 260 may be rotationally fixed to retractor assembly 240. As shown in FIGS. 7A-7C, retractor assembly 240 may rotate and translate together with lead nut 251 and sleeve 260, all relative to screw driver 500, ratchet assembly 230, and lead screw 250. As shown in FIG. 4B, screw driver 500 may be coupled at a proximal end thereof to ratchet body 232, and at a distal end thereof to bone anchor 400 with associated stylet 300 prior to insertion.

Figure 4A:
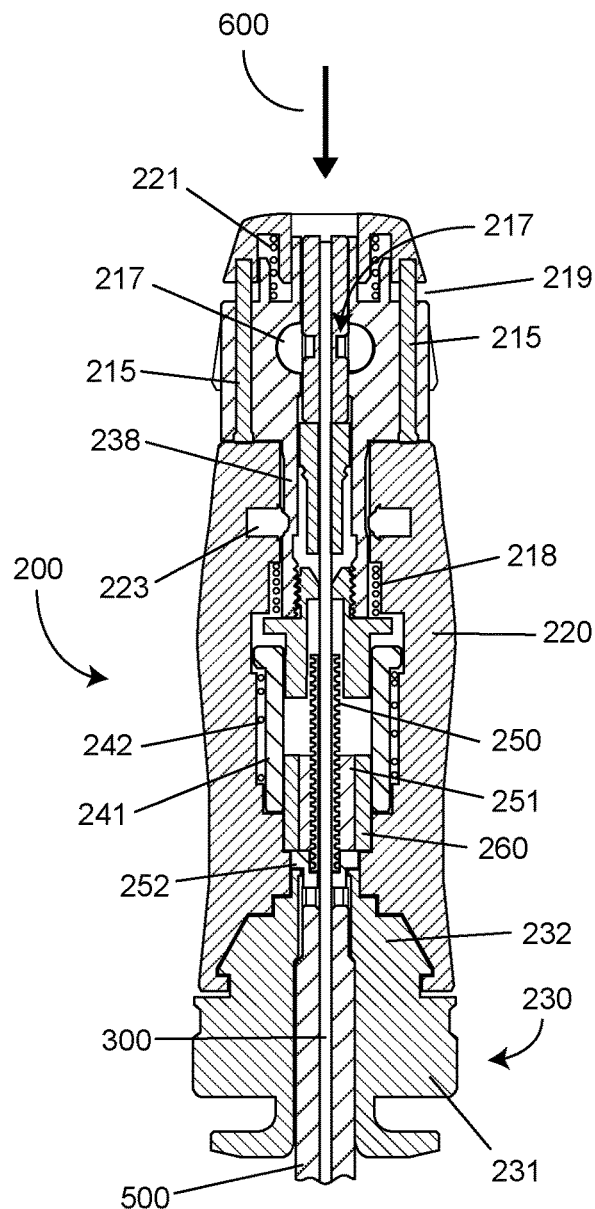
FIG. 4A provides a perspective view of the ratchet retracting handle in a docking mode, according to an embodiment of the invention.
Figure 4B:
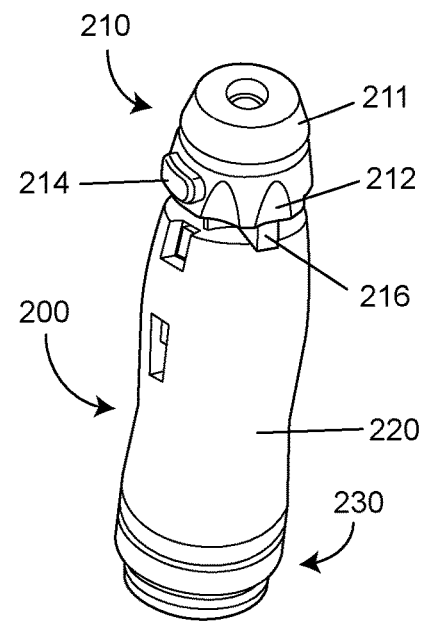
FIGS. 4B-4C provide cross-sectional views of the ratchet retracting handle in a docking mode, according to an embodiment of the invention.
Figure 4C:
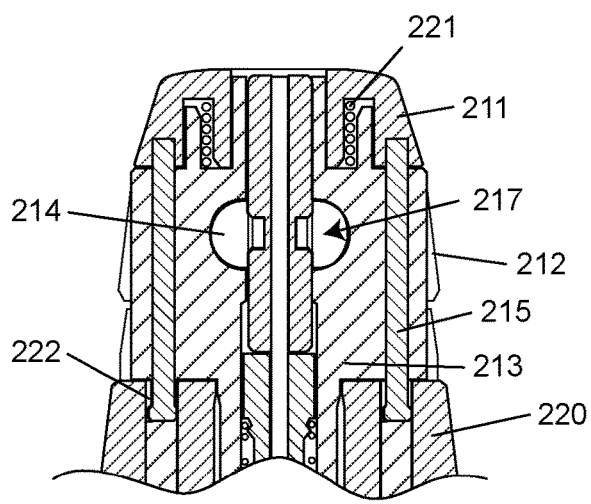

As further shown in FIGS. 4A-4C, a cover 220 may be disposed over and may enclose portions of ratchet retracting handle 200. For example, cover 220 may cover and/or enclose retractor assembly 240, portions of ratchet assembly 230, and a portion of cap assembly 210, e.g., at least a portion of cap body 213. In some embodiments, cover 220 may include a see-through window 224 (FIGS. 2A-2B) as discussed further herein, as well as one or more axially extending slots 222 (FIG. 4B). Each axially extending slot 222 may terminate in an opening at the proximal edge of cover 220, and each slot 222 may be shaped, dimensioned, and positioned to facilitate mating engagement with a retractor post 245 and with a pushing post 215 as discussed further herein. Each retractor post 245 is configured to travel axially within a corresponding slot 222 of the cover 220. The number slots 222 and position of each slot 222, e.g., its circumferential position relative to the proximal end of cover 220, may be determined based on the corresponding number and position of retractor posts 245 and/or pushing posts 215. For example, various embodiments may include two, three, four, or more slots 222 disposed about cover 220. In further embodiments, a ball detent 223 is provided, which travels within axially-extending groove 238 within cap body 213. Ball detent 223 is spring loaded, the force of which can be overcome to allow translation of pins (not shown in FIG. 4B) into fixed positions, thereby providing rotational resistance and tactile feedback. An additional configuration for ball detent 223 is described further herein with respect to FIG. 14.

Cover 220 may be rotationally fixed to retractor assembly 240, although cover 220 and retractor assembly 240 may translate axially relative to one another. As a result, rotation of cover 220 may cause rotation of retractor assembly 240, lead nut 251, and sleeve 260. Rotation of cover 220 in a first direction (e.g., clockwise) may cause rotation of ratchet knob 231 and ratchet body 232 along with cover 220 in the first direction, thereby causing rotation of screw driver 500 and advancement of stylet 300 and bone anchor 400 in a distal direction, e.g., for insertion. Rotation of cover 220 in a second direction opposite the first direction, e.g., a counter clockwise direction, may cause ratchet knob 231 to rotate along with cover 220, while ratchet body 232 does not rotate. The relative rotation in the second direction of ratchet knob 231 relative to ratchet body 232 results in bone anchor 400 and screw driver 500, along with lead screw attachment 252 and lead screw 250 remaining translationally fixed in position, while retractor assembly 240, lead nut 251, sleeve 260, stylet 300, and cap assembly 210 may translate proximally, thereby retracting stylet 300. The gripping force on bone anchor 400 also holds screw driver 500 and bone anchor 400 and prevents these features from rotating at the same time.

In FIGS. 4A-4C, handle 200 is shown in the docking mode. As illustrated, cap assembly 210 may further include biasing element 221 (FIGS. 4B-4C) disposed between cap 211 and knob 212. Biasing element 221 may be, for example, a coil spring. Biasing element 221 biases cap 211 in a proximal direction relative to knob 212, such that cap 211 is separated from knob 212 by gap 219 when biasing element 221 is in its resting state. As long as gap 219 is maintained by biasing element 221, pushing posts 215, which extend distally from cap 211, are prevented from engaging with retractor posts 245 and slots 222.

In the docking mode, one or more legs 216 (FIG. 4A) of cap assembly 210 may abut the distal edge of cover 220, so that knob 212 is translationally fixed at least in a distal direction relative to the cover 220, i.e., knob 212 cannot move further in a distal direction toward cover 220. When a mallet or pushing force 600 is applied on cap 211, cap 211 moves or translates distally relative to knob 212 against the force of biasing element 221 until it is stopped by knob 212, which remains translationally fixed relative to cover 220. During this process, each pushing post 215 may translate to a limited extent into a corresponding slot 222 in cover 220, insufficient to materially engage with retractor posts 245. Stylet 300, which is retained by retention elements 217 in knob 212, may remain translationally fixed to knob 212. Thus, stylet 300 does not move distally even when cap 211 moves distally and abuts knob 212, as shown in FIG. 4C.

Figure 5A:
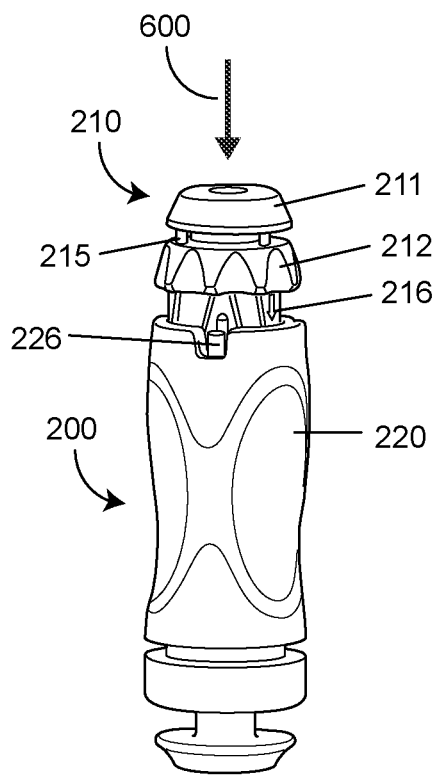
FIG. 5A provides a perspective view of the ratchet retracting handle in the docking mode and beginning the transition to the extended mode, according to an embodiment of the invention.
Figure 5B:
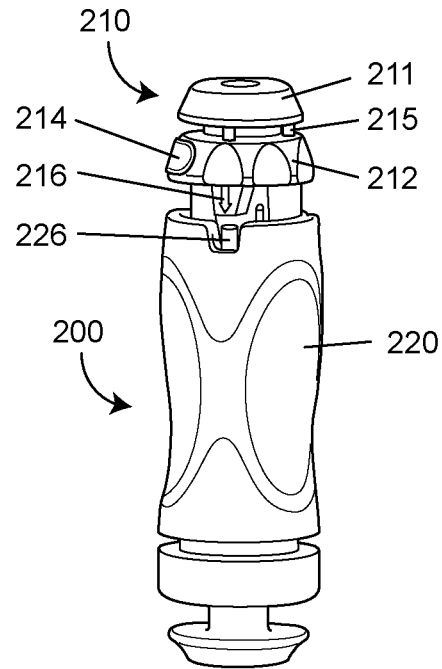
FIG. 5B provides a perspective view of the ratchet retracting handle starting extension of the stylet, according to an embodiment of the invention.
Figure 5C:
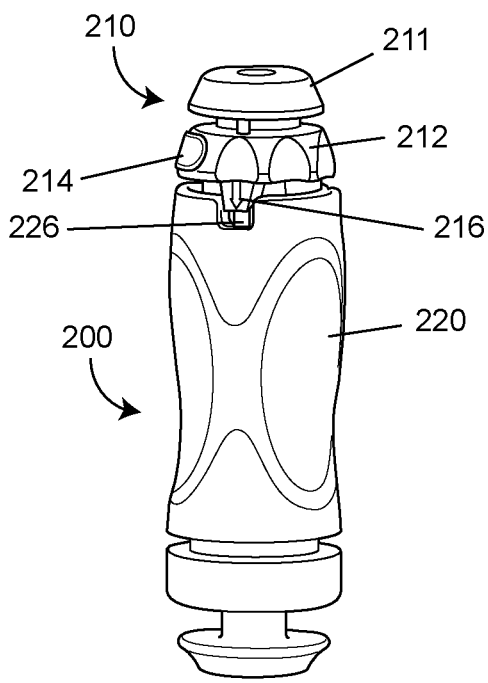
FIG. 5C provides a perspective view of the ratchet retracting handle during extension of the stylet, according to an embodiment of the invention.
Figure 5D:
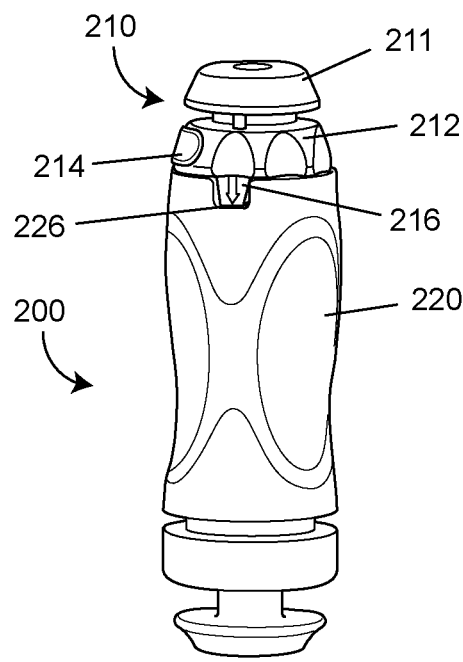
FIG. 5D provides a perspective view of the ratchet retracting handle in the extended mode, according to an embodiment of the invention.
Figure 6C:
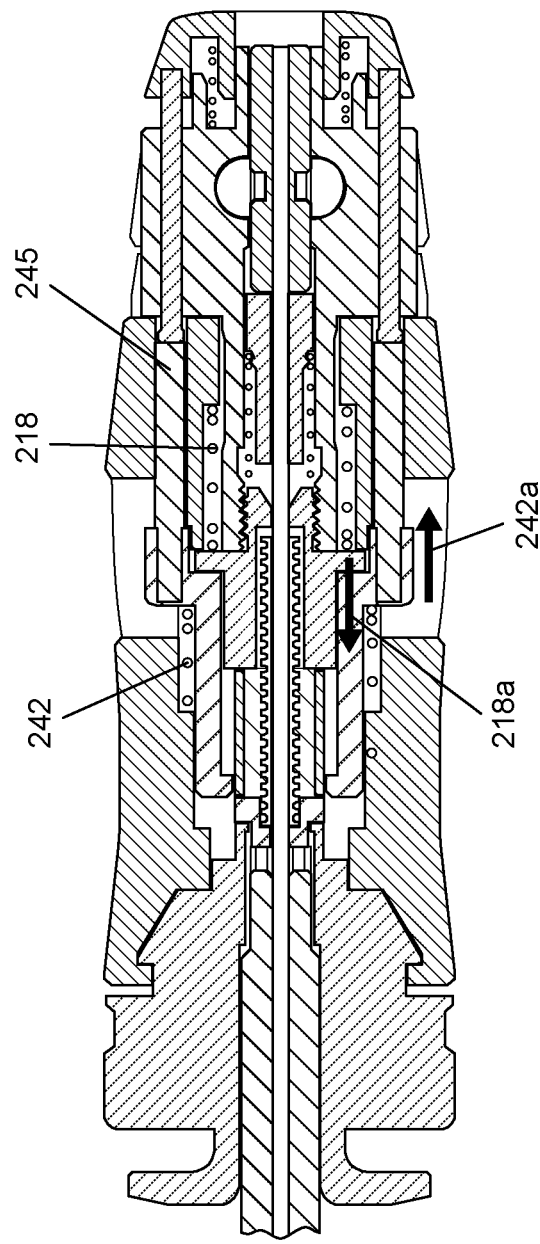
FIG. 6C provides a cross-sectional view corresponding to the perspective view of FIG. 5C, and illustrates the ratchet retracting handle during extension of the stylet, according to an embodiment of the invention.

FIGS. 5A-5D and 6A-6D illustrate the transition from the docking mode to the deployed or extended mode. FIGS. 5A and 6A illustrate ratchet retracting handle 200 in the docking mode prior to beginning the transition to the extended mode. As described above, when mallet force 600 is applied to cap 211 in the docking mode, cap 211 moves distally until a distal edge of leg(s) 216 abuts a proximal edge of cover 220 (FIG. 5A). From this position in FIG. 5A, knob 212 may be turned, e.g., a clockwise or a counterclockwise direction relative to cover 220. This turn brings leg(s) 216 into alignment with extension channel(s) 226 in cover 220. When leg(s) 216 reaches alignment with a corresponding extension channel(s) 226 in cover 220, as shown in FIG. 5B, knob 212 can move further in a distal direction until it abuts the distal edge of cover 220. At this point, a distal surface of knob 212 may make substantially uninterrupted contact, e.g., circumferential contact, with a proximal edge of cover 220. Leg(s)

216 move progressively distally into the corresponding and complementary-shaped extension channel(s) 226 as shown in FIGS. 5C-5D. The stylet 300 that is translationally locked to knob 212 via retention elements 217 (FIG. 4B) thus also moves distally. Cap 211 can also be pushed distally until it contacts knob 212 in a fashion similar to that in the docking mode during or after stylet 300 extension.

Figure 6D:
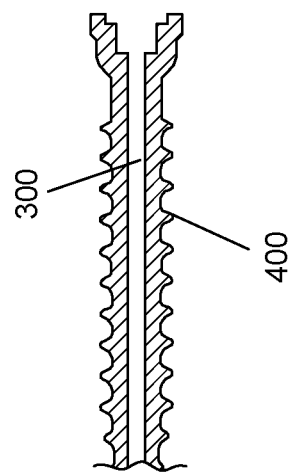
FIG. 6D provides a cross-sectional view of the bone anchor and stylet tip in the extended mode, corresponding to a portion of the perspective view of FIG. 5D, according to an embodiment of the invention.

As knob 212 approaches cover 220 as it moves out of the docking mode of FIGS. 5A and 6A, through the progressive transitional phases depicted in FIGS. 5B and 6B, and 5C and 6C, and into the extended mode of FIGS. 5D and 6D, pushing posts 215 may translate distally in corresponding slots 222 as shown in FIGS. 6B and 6C, achieve contact at their distal ends with the proximal ends of retracting posts 245, and push the retracting posts 245 distally, traveling within the same slots 222. As a result, the distal movement of cap 211 and pushing posts 215 pushes retractor assembly 240 distally as well, as shown in FIG. 6C, and extends stylet 300 in a distal direction beyond bone screw 400 as shown in FIG. 6D. The distance by which stylet 300 extends beyond the distal tip of bone screw 400 in the extended mode may be predetermined for a particular application. In particular, retention elements 217 retain stylet 300 within cap assembly 210, such that the predetermined distance is governed by the distance traveled by cap assembly 210 when malleted.

In some exemplary embodiments, this distance may be, e.g., about 3 mm to about 10 mm, or more particularly, about 3 mm, about 4 mm, about 5 mm, about 6 mm, about 7 mm, about 8 mm, about 9 mm, or about 10 mm, or other distances.

FIG. 6C illustrates in greater detail the balance of forces in the extended mode. In this particular embodiment, advancing force 218a in a distal direction of cap assembly spring 218 is smaller than biasing force 242a in a proximal direction of retractor spring 242. However, the additional gripping force from the bone holding stylet 300 extended may be cumulative with the advancing force 218a. This can balance out or even exceed the retracting force 242a, thereby causing stylet 300 to remain extended.

In some embodiments, the biasing forces are pre-adjusted, taking into consideration the gripping force from the bone that holds stylet 300 extended. For example, the biasing force 218a of cap assembly spring 218 may be smaller than the biasing force 242a of retractor spring 242. In another example, the biasing forces may be adjusted so that the sum of the gripping force and the biasing force 218a of cap assembly spring 218 is equivalent to or slightly larger than the biasing force 242a of retractor spring 242 by about 0.1% to about 15% of the force of retractor spring 242, so as to keep stylet 300 extended. In some embodiments, the biasing forces may be customized for specific applications of stylet 300, different medical procedures, or different patients. For example, the stiffness of the spring may vary with the hardness of the bone into which bone anchor 400 is inserted, such that a harder bone demands a harder or more firm spring, while softer bone does not demand such a firm spring.

Turning back to FIGS. 7A-7C, as previously noted, after insertion of bone screw 400 initiated by rotation of cover 220 in the first direction, cover 220 may then be rotated in a second direction that is opposite the first direction. For example, where the first direction for bone anchor insertion is clockwise, the second direction may be counter clockwise. When cover 220 is rotated in the second direction, ratchet knob 231 (FIG. 7B) may rotate along with cover 220, but ratchet body 232 may not rotate. The gripping force on bone anchor 400 may hold screw driver 500 and bone anchor 400 from rotating or translating distally, but upon rotation of ratchet knob 231 relative to ratchet body 232, retractor assembly 240 and therefore stylet 300 may automatically retract proximally relative to the bone anchor 400. As a result, lead nut 251, sleeve 260, retractor assembly 240, and cap assembly 210 may all rotate and translate proximally together until retractor assembly 240 is stopped, e.g., by a proximal edge of the window 224, or a stopping element 261 (FIG. 8B), e.g., a stopping ledge on cover 220. Thus, cover 220 may rotate but does not translate proximally. Rather, lead nut 251, sleeve 260, retractor assembly 240, and cap assembly 210 rotate and translate proximally together. In some embodiments, the automatic retraction of stylet 300 can be performed using only one hand, providing increased convenience and efficiency for the user.

Figure 8A:
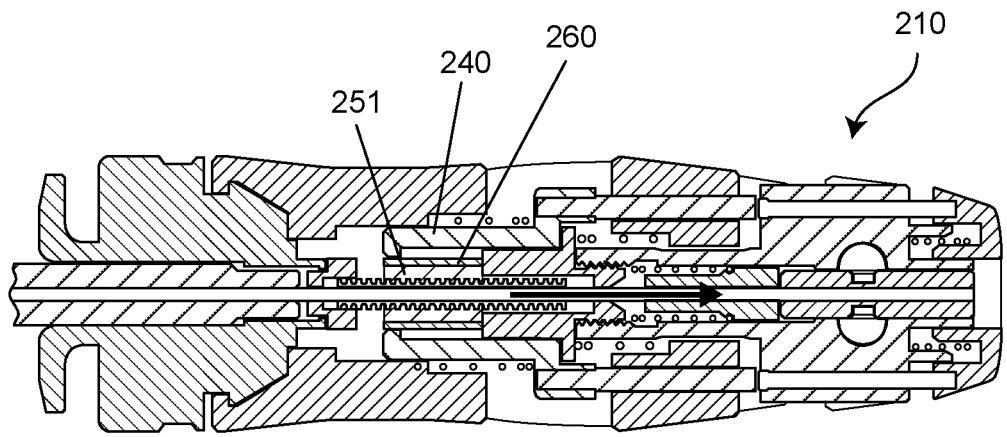
FIG. 8A provides a cross sectional view of the ratchet retracting handle during stylet retraction, according to an embodiment of the invention.
Figure 8B:
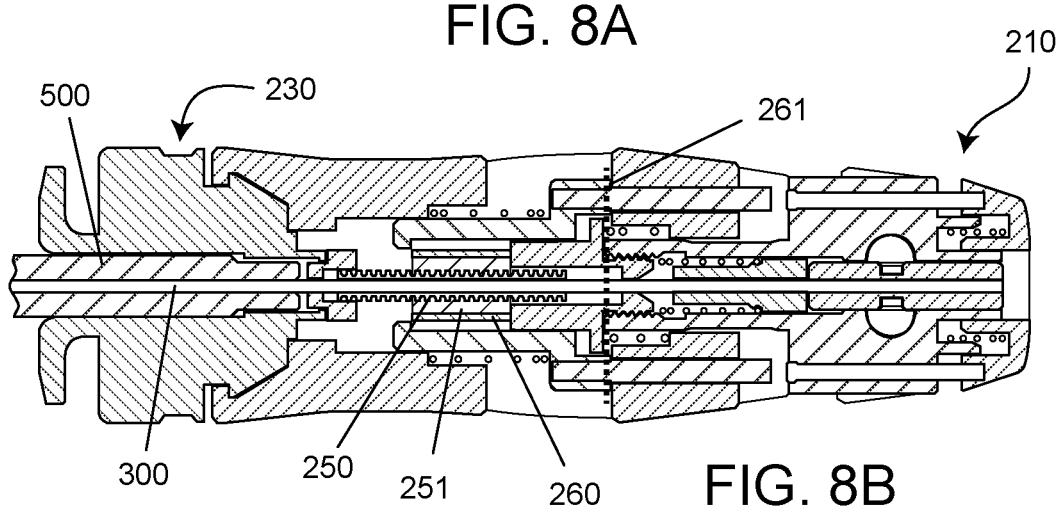
FIG. 8B provides a cross sectional view of the ratchet retracting handle in the extended mode, according to an embodiment of the invention.
Figure 8C:
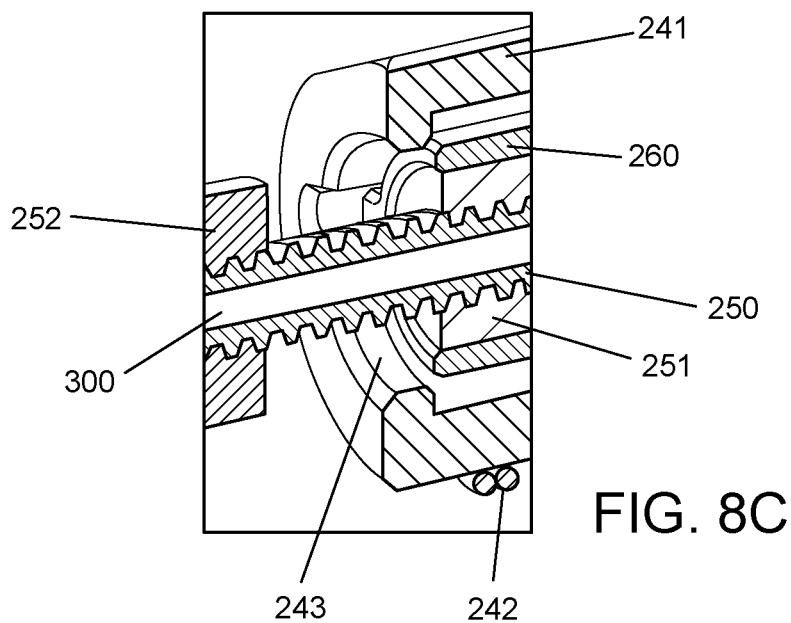
FIG. 8C provides a cutaway view of the ratchet retracting handle in the extended mode, according to an embodiment of the invention.

FIG. 8A shows, in a particular embodiment, that retractor assembly 240, cap assembly 210, lead nut 251, and sleeve 260 all translate proximally relative to cover 220 and ratchet assembly 230. FIG. 8B shows at the end of the retraction process, progress in the proximal direction of retractor assembly 240 is stopped, and retractor assembly 240 abuts a stop element 261 on cover 220, in this case, the distal edge of window 224 on cover 220. FIG. 8C is an enlarged view showing sleeve 260 and lead nut 251, which are free to rotate after they retract along with stylet 300, and move away from groove 243 at a distal end of retractor body 241. Rotation of lead nut 251 and sleeve 260 within the cavity of retractor body 241 as shown in FIG. 8C may allow uninterrupted screw 400 insertion after stylet retraction.

The proximal translation of lead nut 251, retractor assembly 240, and cap assembly 210 may cause retraction of stylet 300 for a predetermined or customized distance. For example, it can be within a predetermined range or a fixed value. As a non-limiting example, the retractable distance may be large enough so that the tip of stylet 300 is retracted out of the patient. In various embodiments, the retractable distance is in a range of about 0.1 mm to about 7 mm, a range of about 5 mm to about 12 mm, or a range of about 5 mm to about 15 mm. The foregoing ranges are merely illustrative and are intended to be combinable, e.g., to include about 0.1 mm to about 12 mm, about 0.1 mm to about 15 mm, and to include all distances within the foregoing ranges including, e.g., about 0.1 mm, about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm.

As discussed above, cover 220 may include a see-through window 224 thereon (FIGS. 2A-2B), which may provide a visual indication and/or visual confirmation of retraction of stylet 300. In some cases, at least a part of retractor body 241 may be visible in see-through window 224. In further embodiments, at least a part of retractor body 241 may extend radially outwardly into see-through window 224, thereby constraining or eliminating rotational movement of retractor assembly 240 relative to cover 220. As described herein, cover 220 may be rotationally fixed relative to retractor assembly 240, rotatable relative to ratchet assembly 230, translationally fixed relative to ratchet assembly 230, and translatable relative to retractor assembly 240.

Figure 9A:
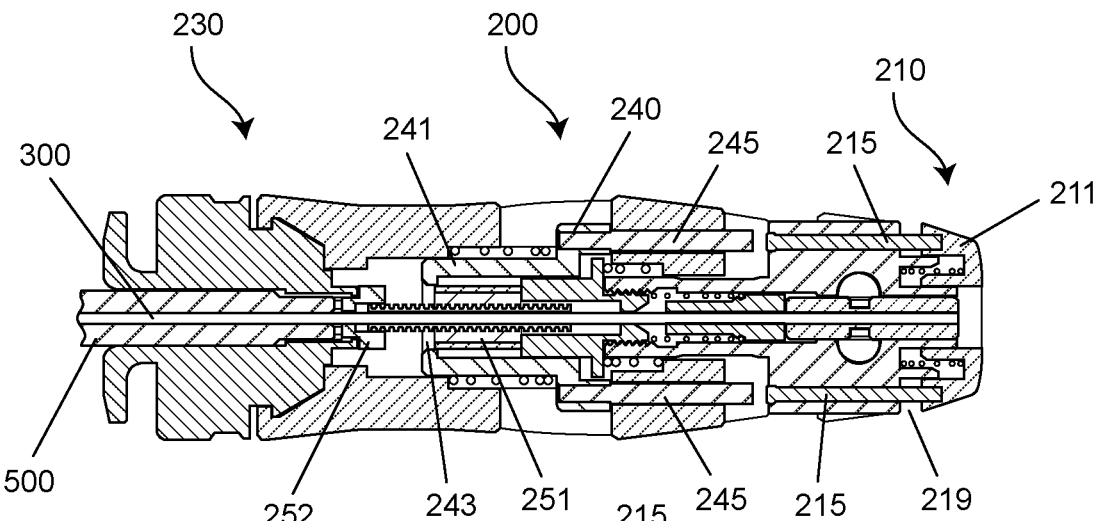
FIG. 9A provides a cross sectional view of the ratchet retracting handle starting to reset and repeat extension of the stylet, according to an embodiment of the invention.
Figure 9B:
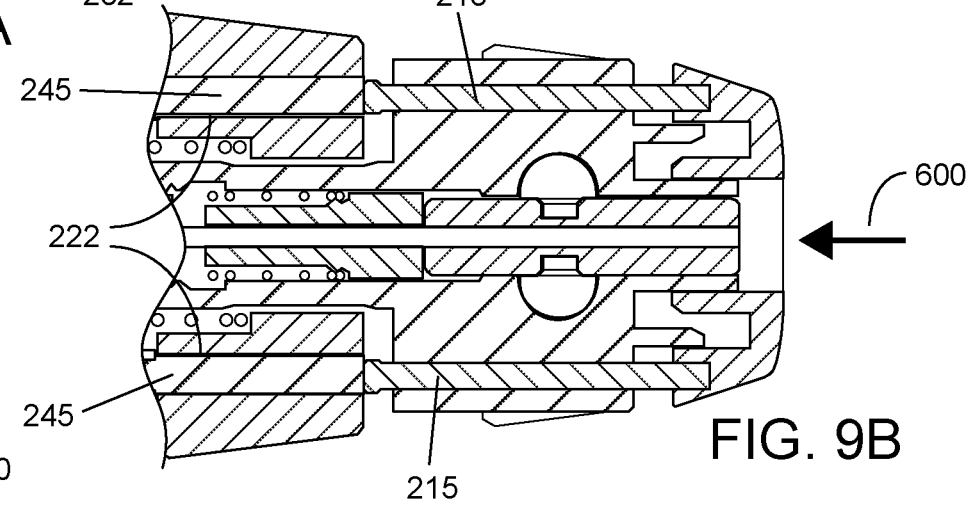
FIG. 9B provides a cross sectional view of a portion of the ratchet retracting handle after resetting, according to an embodiment of the invention.
Figure 9C:
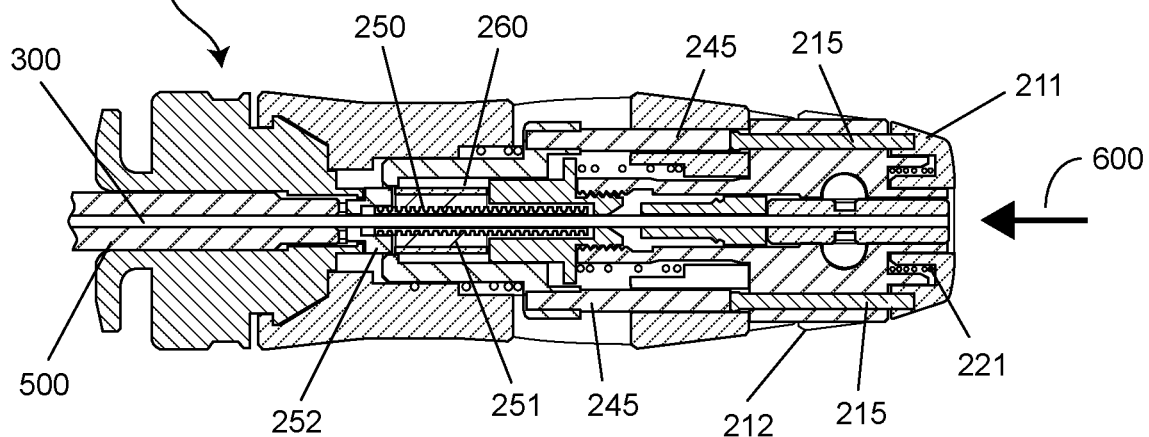
FIG. 9C provides a cross sectional view of the ratchet retracting handle after resetting, according to an embodiment of the invention.

Turning to FIGS. 9A-9C, embodiments are depicted in which ratchet retracting handle 200 may be reset to extend again subsequent to the retraction of stylet 300. After retraction of stylet 300, cap 211 and knob 212 can be re-aligned so that leg(s) 216 (FIGS. 5A-5C) can again move into extension channel(s) 226 (FIGS. 5A-5C). A pushing force in a distal direction (FIG. 9B) may be applied to the proximal end of cap 211, causing pushing posts 215 on cap 211 to engage first with posts 245 of retractor assembly 240, before cap assembly 210 pushes on lead nut 251. This can be ensured by gap 219 between cap 211 and knob 212, which ensures that pushing post(s) 215 and retractor post(s) 245 contact first. When pushing posts 215 of cap 211 contact retractor posts 245 of retractor assembly 240, retractor assembly 240 can be pushed distally. As cap assembly 210 moves distally, force is applied in a distal direction by cap assembly 210 on lead nut 251, which may cause lead nut 251 to rotate and advance distally on the threads of lead screw 250. Lead nut 251 may rotate and advance until it falls back into grooves 243 of retractor body 241. Ratchet retracting handle 200 is then reset and ready for a new screw 400 insertion and/or stylet 300 retraction.

As described herein, ratchet retracting handle 200 herein may extend and/or automatically retract a stylet 300 associated with a bone anchor 400 to be inserted. In the docking mode, stylet 300 may extend beyond the distal tip of bone screw 400 for a first distance. The first distance may be, e.g., about 3 mm, or any value in the range of about 0.1 to about 10 mm. In the extended mode, distal movement of cap 211 and knob 212 may cause stylet 300 to be extended further beyond a distal tip of bone screw 400 for a pre-determined second distance into a bone. For example, the pre-determined second distance is about 0.1 mm to about 7 mm. Thus, if the first distance, between the tip of stylet 300 in the docking mode to the tip of the bone screw 400, is 3 mm, and the second distance it can be further extended by a second distance of another 7 mm in the extended mode, the tip of stylet 300 may be extended a cumulative 10 mm beyond the distal tip of bone screw 400. Ratchet retracting handle 200 advantageously allows stylet 300 to be retracted either in the docking mode or in the extended mode.

Referring to FIGS. 10A-10B and 11A-11B, ratchet retracting handle 200 is illustrated in a number of positions discussed herein. FIGS. 10A-10B illustrate ratchet retracting handle 200 in the extended mode with stylet 300 extended and retracted, respectively, while FIGS. 11A-11B illustrate ratchet retracting handle 200 in the docking mode with stylet 300 extended and retracted, respectively.

As shown in FIGS. 12A-12B, further embodiments may additionally include housing element 246 (FIG. 12A). Housing element 246 may be rotationally and translationally fixed to the cover 220, and it may be rotationally fixed to retractor assembly 240 and translatable relative to retractor assembly 240. In some embodiments, housing element 246 may be a rigid element that contains the components therein including, e.g., retractor assembly 240, retractor spring 242, a portion of cap body 213, cap assembly spring 218, etc. In embodiments in which housing element 246 provides structure and rigidity to support and retain these components, cover 220 may be made of a softer, less rigid material such as, e.g., a silicon over mold. In embodiments in which housing element 246 is not present, the rigidity may instead be provided by cover 220 itself. Thus, embodiments with and without housing element 246 may function similarly.

Figure 14:
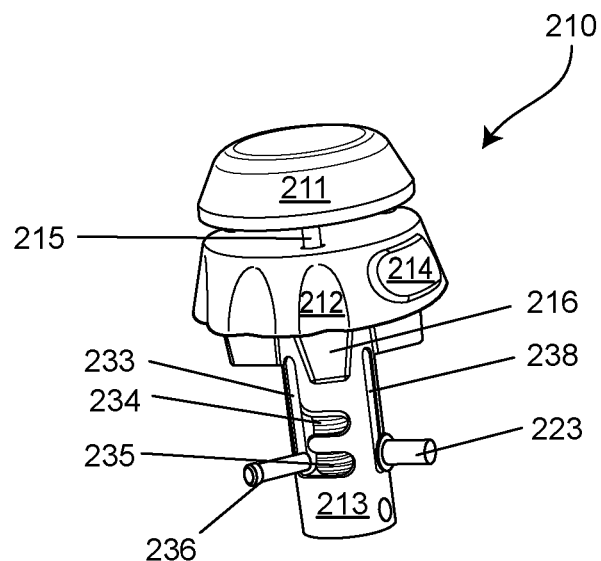
FIG. 14 provides a perspective view of the cap assembly of a ratchet retracting handle, according to an embodiment of the invention.

Still further, additional features of cap assembly 210, present in certain embodiments, are illustrated in FIG. 13, and in greater detail in FIG. 14. In such embodiments, cap body 213 may include a first groove 233 which runs axially along an outer surface of cap body 213. First groove 233 further includes a first horizontal portion 234 and a second horizontal portion 235. A pin 236 is provided, which translates along first groove 233, and may be fixed in position within first horizontal portion 234 or second horizontal portion 236. Cap body 213 may also include a second groove 238, which runs axially along an outer surface of cap body 213, which may be radially spaced from first groove 233. A ball detent or ball plunger 223 may be provided, which may be movable in and out of second groove 238, and may travel axially within second groove 238 within cap body 213. Ball detent 223 may be spring loaded, the force of which may be overcome to allow translation of pin 236 into fixed positions, e.g., within first horizontal slot 234 or second horizontal slot 235. Ball detent 223 provides rotational resistance and tactile feedback, and pops in and out of second groove 238 channel as cap body 213 is rotated.

Also disclosed herein are methods for automatically retracting a stylet associated with a bone anchor during insertion of the bone anchor. Methods according to such embodiments may include one or more operations as disclosed herein. For example, such methods may include providing a ratchet retracting handle as disclosed herein to a user. The ratchet retracting handle can be coupled to a driver for inserting the bone anchor. The method may include, when in the docking mode or extended mode, retracting the stylet proximally by rotating the cover relative to the ratchet assembly using only one hand, while holding the driver and the bone screw rotationally and translationally fixed relative to the ratchet assembly. The method may further include causing the retractor assembly, the cap assembly, and the lead nut to translate proximally by rotating the cover, thereby retracting the stylet that is locked to the cap body.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "approximately," "generally," and "substantially" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, +/−16%, +/−17%, +/−18%, +/−19%, or +/−20%, depending on the embodiment. As a further non-limiting example, about 100 millimeters represents a range of 95 millimeters to 105 millimeters, 90 millimeters to 110 millimeters, or 85 millimeters to 115 millimeters, depending on the embodiments.

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A ratchet retracting handle for automatically retracting a stylet during insertion of a bone anchor, the ratchet retracting handle comprising:
    a cap assembly translationally fixed to the stylet, wherein the cap assembly comprises:
        a cap body;
        a knob coupled to and disposed proximally relative to the cap body; and a cap matingly engaged with a proximal end of the knob;

a retractor assembly engaged with the cap assembly and disposed distally thereof, wherein the retractor assembly comprises a retractor body and two or more retractor posts extending proximally therefrom, and wherein engagement of the retractor assembly with the cap assembly produces translational movement of the retractor assembly in a distal direction;

a ratchet assembly coupled to a distal end of a lead screw and to a proximal end of a screw driver; and a cover disposed over at least part of each of the ratchet assembly, the retractor assembly, and the cap assembly, the cover further being rotationally fixed to the retractor assembly, wherein the knob is rotatable and translatable relative to the cover, to move between a first, docking mode, and a second, extended mode, wherein rotation of the cover in a first direction is configured to advance the stylet and the bone anchor distally, and wherein the rotation of the cover in a second direction opposite the first direction is configured to retract the retractor assembly and the stylet proximally relative to the bone anchor, while the bone anchor is restrained from rotating.

2. The ratchet retracting handle of claim 1, wherein, in the docking mode, the knob is translationally fixed at least in the distal direction relative to the cover, and wherein the cap is movable relative to the knob at least in the distal direction, and the stylet is fixed translationally relative to the knob at least in the distal direction when the cap moves distally toward the knob.

3. The ratchet retracting handle of claim 1, wherein the cap assembly further comprises a leg, and wherein in the docking mode, the leg is configured to abut a distal edge of the cover, and wherein, in the extended mode, the knob is configured to rotate to align the leg with a complementary shaped extension channel disposed on a proximal end of the cover, such that the leg engages with the complementary shaped extension channel, thereby causing distal movement of the knob relative to the cover.

4. The ratchet retracting handle of claim 3, wherein, in the extended mode, the cap is movable relative to the knob in the distal direction, and wherein distal movement of the knob causes the stylet to be extended distally, beyond a distal tip of the bone anchor for a pre-determined distance.

5. The ratchet retracting handle of claim 4, wherein the pre-determined distance is about 0.1 mm to about 7 mm.

6. The ratchet retracting handle of claim 1, wherein the cap assembly further comprises two or more pushing posts extending distally from the cap, wherein the two or more pushing posts are evenly spaced with respect to one another about a circumference of the cap.

7. The ratchet retracting handle of claim 6, wherein the two or more pushing posts further comprises three pushing posts.

8. The ratchet retracting handle of claim 6, wherein the cover further comprises two or more axially extending slots therein, wherein each of the axially extending slots terminates in an opening at a proximal edge of the cover, and wherein, in the extended mode, each of the two or more pushing posts is configured to translate through the opening and into a corresponding axially extending slot in the cover.

9. The ratchet retracting handle of claim 1, wherein the retractor assembly comprises a retractor spring disposed about the retractor body, the retractor spring being biased to retract the stylet in a proximal direction.

10. The ratchet retracting handle of claim 1, further comprising a cap assembly spring disposed on the cap body, wherein the cap assembly spring is configured to bias the stylet in the distal direction relative to the cap assembly, thereby advancing the stylet in the distal direction.

11. The ratchet retracting handle of claim 8, wherein each of the two or more retractor posts is aligned with, and is translatable within a corresponding one of the two or more axially extending slots in the cover.

12. The ratchet retracting handle of claim 11, wherein the two or more pushing posts are configured to translate distally and push in the distal direction on the two or more retractor posts within the corresponding axially extending slots in the cover, causing the retractor assembly to translate distally.

13. The ratchet retracting handle of claim 12, wherein the cap assembly further comprises:

a biasing element disposed between the cap and the knob, the biasing element being configured to bias the cap in a proximal direction, away from the knob, such that a gap is maintained between the cap and the knob in an absence of force applied to a proximal end of the cap, wherein the gap is closable by an application of force to the proximal end of the cap, and wherein the application of force to the proximal end of the cap causes contact between the pushing posts and the retractor posts within the slots.

14. The ratchet retracting handle of claim 1, further comprising:

a lead nut disposed over, and in threaded engagement with the lead screw; and a sleeve disposed over the lead nut, wherein the lead nut and the sleeve are rotationally fixed with respect to the retractor assembly, and wherein the rotation of the cover in the first direction causes rotation of the retractor assembly, the ratchet assembly, and the screw driver, and wherein the rotation of the cover in the second direction causes rotation of the retractor assembly, rotation and translation of the lead nut and the sleeve, and does not cause rotation of the screw driver or the ratchet assembly, thereby retracting the stylet for a retraction distance.

15. The ratchet retracting handle of claim 14, wherein the retraction distance is in a range of about 0.1 mm to about 12 mm.

16. The ratchet retracting handle of claim 1, wherein the stylet is associated with the bone anchor, and a distal tip of the stylet extends beyond a distal tip of the bone anchor by a distance of about 0.1 to about 3 mm in the docking mode, and about 3 mm to about 10 mm in the extended mode.

17. The ratchet retracting handle of claim 1, wherein the cover further comprises a stopping element disposed on an inner surface thereof, the stopping element being configured to define a maximally retracted position of the retractor assembly and the stylet.

18. The ratchet retracting handle of claim 1, wherein the cover further comprises a see-through window thereon, wherein the see-through window is configured to provide a visual indication of retraction of the stylet, and wherein at least a part of the retractor body is visible through the see-through window.

19. The ratchet retracting handle of claim 2, further comprising:

a retention element disposed within the knob, configured to selectively and releasably retain the stylet in a translationally fixed position, and a retention button disposed on the knob, configured to operably control the retention element.

20. The ratchet retracting handle of claim 9, further comprising an annular member disposed about the retractor body distally relative to the retractor spring, wherein the annular member is configured to limit binding of the retractor spring during operation.

\* \* \* \* \*